United States Patent [19]

Weiss

[11] 4,113,967
[45] Sep. 12, 1978

[54] 15,16-DIOXY PROSTENOIC ACIDS AND ESTERS

[75] Inventor: Martin Joseph Weiss, Oradell, N.J.

[73] Assignee: American Cyanamid Company, Stamford, Conn.

[21] Appl. No.: 767,863

[22] Filed: Feb. 11, 1977

Related U.S. Application Data

[63] Continuation-in-part of Ser. No. 663,603, Mar. 3, 1976, abandoned.

[51] Int. Cl.$^2$ .......................................... C07C 177/00
[52] U.S. Cl. .............................. 560/121; 260/340.9 P; 260/345.9 P; 260/438.1; 260/448.8 R; 424/305; 424/317; 562/503; 568/855; 568/838
[58] Field of Search .................... 260/514 D; 560/121

[56] References Cited

PUBLICATIONS

Bornatsch et al., Prostaglandins, 14, 617(1977).

Primary Examiner—Robert Gerstl
Attorney, Agent, or Firm—Charles F. Costello, Jr.

[57] ABSTRACT

This disclosure describes novel erythro 15,16-dioxy prostenoic acids and esters useful as bronchodilators, hypotensives and gastric acid secretion inhibitors.

17 Claims, No Drawings

15,16-DIOXY PROSTENOIC ACIDS AND ESTERS

CROSS-REFERENCE TO RELATED APPLICATIONS

This application is a continuation-in-part of our co-pending application, Ser. No. 663,603, filed Mar. 3, 1976 now abandoned.

FIELD OF THE INVENTION

This invention relates to optically active erythro 15,16-dioxy prostenoic acids and esters of the formula:

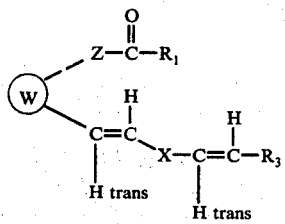

wherein
W is selected from the group comprising

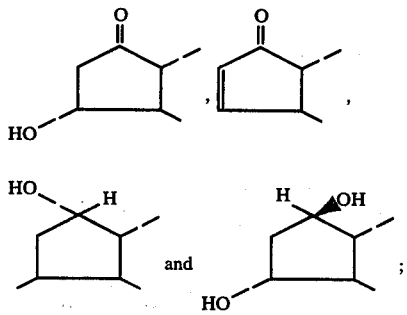

$R_1$ is selected from the group comprising hydroxy, and $C_1$–$C_5$ alkoxy;
$R_3$ is methyl, ethyl and propyl;
X is a divalent radical of the formula:

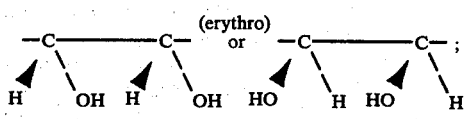

Z is a divalent radical selected from the group comprising —$(CH_2)_6$,

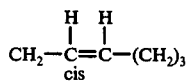

and when $R_1$ is hydrogen the pharmaceutically acceptable salts thereof and the racemic mixture thereof.

BACKGROUND AND DESCRIPTION OF THE INVENTION

Useful pharmacologically acceptable salts of the above formula wherein $R_1$ is hydroxy are those with pharmacologically acceptable metal cations, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are the methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds of this invention are administered in various ways for various purposes, e.g., intravenously, intramuscularly, subcutaneously, orally, intravaginally, rectally, bucally, sublinqually, topically and in the form of sterile implants for prolonged action, and as aerosol inhalants.

For intravenous injection or infusion, sterile aqueous isotonic solutions are preferred. For that purpose, it is preferred because of increased water solubility that $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixers, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain ocassions it may be advantageous to administer the compounds of this invention as clathrate compounds with substances such as β-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom et al., *J. Biol. Chem.*, 238, 3555 (1963) and Horton, *Experientia*, 21, 113 (1965) and references cited therein. All of the so called natural prostaglandins are derivatives of prostanoic acid:

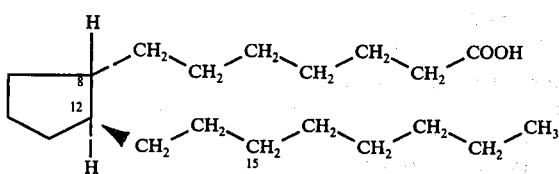

The hydrogen atoms attached to C-8 and C-12 are in trans-configuration. The natural prostaglandins represent only one of the possible optical isomers. The compounds of this invention include all possible optical isomers.

The $C_{15}$ position is a particularly important one and when it is substituted by a hydroxy it is assymetric, with the possibility of two configurations, deemed S or R. In partial formulae (A) below is shown in "natural" configuration of $C_8$, $C_{12}$, and $C_{15}$ as it is found in all known mammallian prostaglandins. The configuration at $C_8$ and $C_{12}$ is referred to as l and at $C_{15}$ as S or $\gamma$; thus formula (A) is the l 15(S) or nat form. The enantiomer of (A) is represented by partial formula (B), the d 15(R) or ent form, and a substance deemed a dl-racemate without designation with regard to the situation at $C_{15}$ consists of enantiomers (A) and (B). Partial formula (C) represents a structure wherein the configuration at $C_8$ and $C_{12}$ is as in (A), the l form, but the configuration at $C_{15}$ is inverted to the R form. A structure embracing the configuration at $C_8$, $C_{12}$, and $C_{15}$ as shown in (C) is referred to as an l 15-epi derivative, the enantiomeric structure is represented by partial formula (D), the d 15-epi derivative, and (C) and (D) constitutes a dl-15-epi racemate.

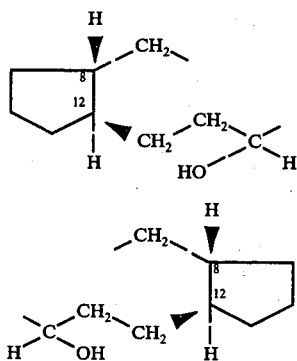

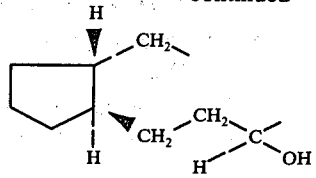

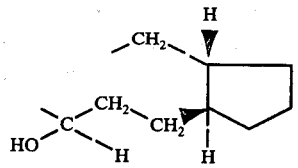

The compounds of this invention include all possible antipodes and particularly both possible configurations for $C_{15}$.

$C_{16}$ of the compounds of this invention is also an assymetric carbon atom and this invention embraces both the R and S configurations at $C_{16}$. When the oxy substituents at $C_{15}$ and $C_{16}$ are to each other as in (E) they are in the erythro configuration, and its mirror image; threo refers to a relationship as in (F) and its mirror image.

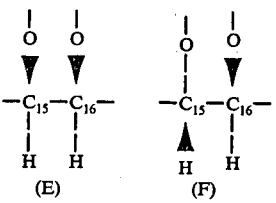

The novel compounds of this invention can be prepared by the reaction sequences illustrated in the following Flowsheets, wherein $R_3$, and Ra are as hereinbefore defined and Rc is a lower alkyl group of from 1 to 3 carbon atoms, inclusive.

The key reaction of these sequences is the conjugate 1,4-addition by an organometallo derivative of $\beta$-chain ($C_{13}$–$C_{20}$) to a 4-unsubstituted or 4-oxycyclopent-2-en-1-one substituted at the 2-position with the $\alpha$-chain ($C_1$–$C_7$). The preparation of the $\beta$-chain required for this synthesis is described in Flowsheet A, which follows.

FLOWSHEET A

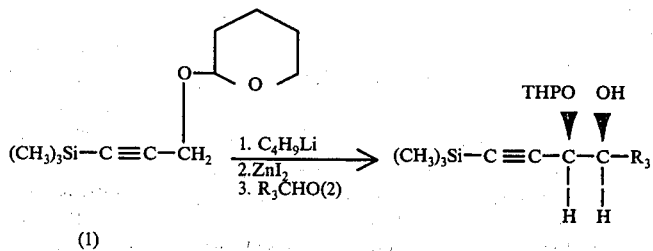

FLOWSHEET A

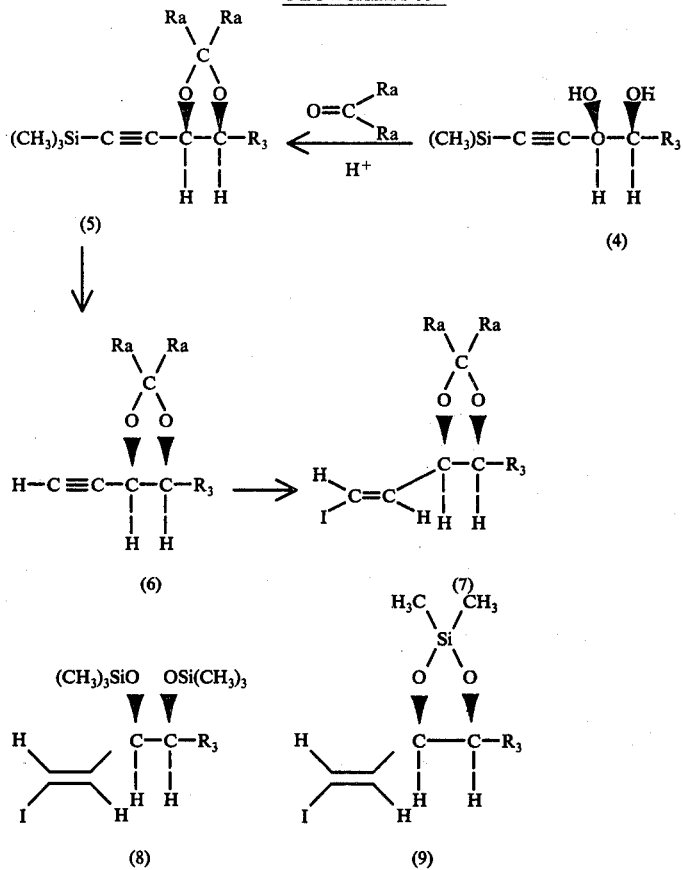

In accordance with the scheme as outlined hereinabove in Flowsheet A, 1-trimethylsilyl-3-tetrahydropyranyloxy-1-propyne (1) is treated with n-butyllithium at −78° C. and then with a freshly prepared solution of zinc iodide in anhydrous tetrahydrofuran, also at −78° C. Reaction of aldehyde (2) with the resulting reagent then provides the 4-hydroxy-3-tetrahydropyranyloxy-1-alkyne (3). This reaction procedes with great stereoselectivity and the product (3) is in the erythro configuration. [For additional information concerning this reaction see the examples which follow and F. Mercier, R. Epsztein and S. Holland, *Bull. Soc. Chim. France,* 690(1972).]

The tetrahydropyranyl group in (3) is removed on weak acid treatment and the resulting erythro diol (4) can be reblocked by treating with an appropriate aldehyde or ketone

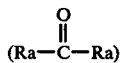
(Ra—C—Ra)

in the presence of strong acid catalyst in the usual way to give the ketal or acetal (5). Acetone is a useful ketone for this purpose and the product (5) is then a 3,4-isopropylidenedioxy-1-alkyne. It is also possible to utilize silyl blocking groups (introduced after removal of the 1-trimethylsilyl group) to ultimately give the vinyl iodides (8) or (9). Weak base treatment of (5), for example heating for about 1 hour in refluxing methanol with potassium carbonate, results in desilylation to give (6). The 1-alkyne (6) is converted to the corresponding 1-iodo-trans-1-alkene (7) by treatment with disiamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give (7).

Conversion of the 1-iodo-trans-1-alkenes (7), (8), (9), or their equivalents of Flowsheet A (see 26 of Flowsheet B) to organometallo derivatives and their conjugate addition to appropriate cyclopentenones is illustrated in Flowsheet B, wherein M is a divalent radical of the group consisting of the following radicals in the erythro configuration:

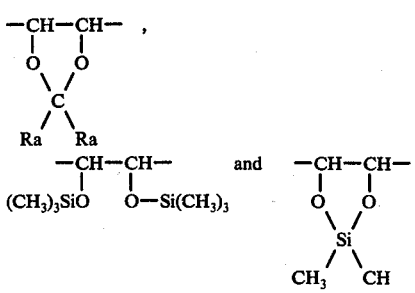

wherein
Ra is as hereinabove defined;
R′₁ is lower alkoxy, tetrahydropyranyloxy or triloweralkylsilyloxy;
R′₂ is tetrahydropyranyloxy or triloweralkylsiloxy;

FLOWSHEET B

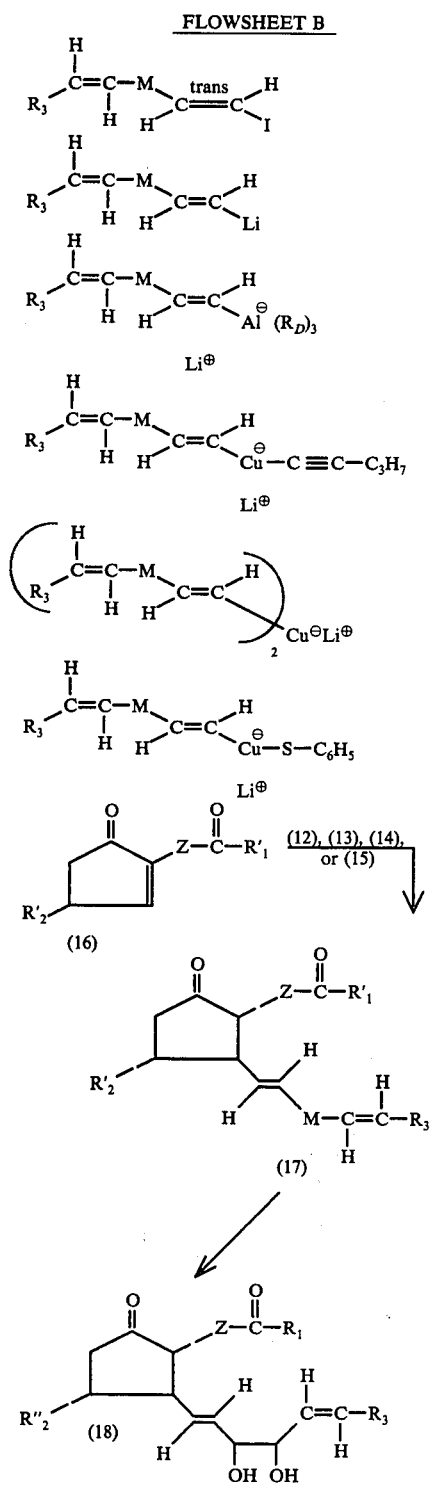

In accordance with the equations of Flowsheet B above, the 1-iodo-1-trans-1-alkene (10) is converted to the trans-vinyl lithium derivative (11) with clean retention of configuration by treatment at about −78° C. in hexane (isomeric mixture solution with either one equivalent of n-butyl lithium or two equivalents of t-butyl lithium. It is preferable for this treatment to proceed for about 1 hour at −78° C., then for about 1 hour at −40° C. and finally for about 1 hour at about 0° C. For the subsequent preparation of lithio alanate reagents (12) it is preferable to use n-butyl lithium, and for the lithio cuprate reagents (13), (14) or (15) t-butyl lithium, is the agent of choice.

For the preparation of the alanate reagent (12) or the like, a molar equivalent of a tri-lower alkyl (1–5 carbon atoms) aluminum (e.g., trimethyl aluminum), dissolved in a solution such as hexane, is added to the vinyl lithium derivative (11) at about 0° C. (It is preferable to avoid use of a tetrahydropyranyl blocking group in the alanate reagent.) After about 15–45 minutes at this temperature the requisite blocked cyclopentenone (16) is added and the reaction mixture is stirred for about 18 hours at ambient temperatures. The mixture is quenched with aqueous dilute hydrochloric acid in the cold and the product is obtained by extraction. Trialkylsilyl blocking groups are removed on treatment with acetic acid:tetrahydrofuran:water (4:2:1) at room temperatures for about 20 minutes. Such treatment does not cleave the ketal/acetal or tetrahydropyranyloxy groups. The silyl, and or tetrahydropyranyl and acetal or ketal groups are removed by treatment with acetic acid:water:tetrahydrofuran (20:10:3) at about 40° C. for about 4 hours to give (18). Alkyl esters of the 11-oxy series are not disturbed by this treatment and cannot be saponified by chemical means in view of the instability of the 11-hydroxy-9-ketone to base treatment. However, the ester can be cleaved by treatment with Baker's Yeast, a procedure well-known in the art.

For the preparation of the assymetric lithio cuprate (13) or the like, a solution of one molar equivalent of copper (I)-1-alkyne, preferably copper (I)-1-pentyne in anhydrous hexamethylphosphorous triamide, preferably three to five molar equivalents, and anhydrous ether is added to one molar equivalent of the aforementioned vinyl lithium (11) solution cooled to about −78° C. After about 1 hour at this temperature, a molar equivalent of the requisiste cyclopentenone (16) is added. After several hours at about −25° C. the reaction mixture is quenched with aqueous ammonium chloride solution and the blocked product (17) is isolated in the usual manner. The deblocking of this product is then carried out in the manner as described hereinabove. The phenylthio cuprate (15) is prepared from lithio thiophenoxide (1 equiv.) and one equivalent of cuprous (I) iodide tri-n-butylphosphine complex, mixed in ether and added at −78° C. to the alkenyl lithio derivative (11).

For the preparation of the symmetrical lithio cuprate (14) one molar equivalent of copper (I) iodide tributylphosphine complex dissoved in anhyrous ether is added at about −78° C. to two molar equivalents of the aforementioned vinyl lithium (11) solution in hexanes, cooled to −78° C. After about 1 hour at this temperature, the lithio cuprate (14) is treated with the requisite cyclopentenone (16) as described hereinabove for the conjugate addition with the 1-alkynyl lithio cuprate (13). For pertinent background information concerning various procedures for carrying out the conjugate addition reaction with lithio cuprate see C. J. Sih et al., *Journ. Amer. Chem. Soc.*, 97, 857 865 (1975).

In order to ensure a trans-relationship in (17) or (18), these products can be submitted to conditions known in the literature to equilibrate cis 8-iso-PGE$_1$ to a mixture containing about 90% of the trans--product [see E. G. Daniels et al., *Journ. Amer. Chem. Soc.*, 90, 5894 (1968)]. These conditions involve treatment with potassium acetate in aqueous methanol for about 96 hours at room temperature. The cis and trans products are separable by chromatographic procedures.

Most of the cyclopentenones required for the purposes of this invention have been described in the literature or can be prepared by procedures quite analogous to those already described. Appropriate references are provided in the examples which follow. The synthesis of certain non-reference requisite cyclopentenones is also described therein.

As illustrated in Flowsheet C below, treatment of the 11-hydroxy derivatives represented by formula (18) in which $R''_2$ is hydroxy with dilute acid results in dehydration of the $\beta$-ketol system and the formation of the corresponding $\Delta^{10}$ derivatives (19) (prostaglandins of the A type). A preferred procedure involves treatment in tetrahydrofuran: water (2:1) solvent 0.5 N in hydrochloric acid for about 20 hours at ambient temperatures.

FLOWSHEET C

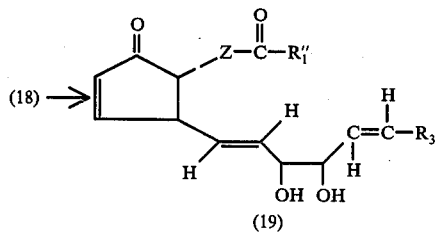

(19)

As illustrated in Flowsheet D below the 9-keto derivatives (20, see 18) of this invention can be converted to the corresponding 9-hydroxy derivatives. If this conversion is effected with sodium borohydride, the product is a mixture of 9α- and 9β-hydroxy derivatives (prostaglandins of the Fα and Fβ series, respectively): (21) and (22), respectively. The 9α and 9β derivatives are separable from each other by chromatographic procedures well-known in the art.

When the reduction is carried out with lithium perhydro-9b-boraphenalyl hydride [H. C. Brown and W. C. Dickason, *Journ. Amer. Chem. Soc.*, 92, 709 (1970)] or with lithium tri(sec butyl)borohydride [H. C. Brown and S. Krishnamwrthy ibid. 94, 7159 (1972)], the product is at least predominantly the 9α-hydroxy derivative (21), wherein the 9-hydroxy group is cis to the sidechain attached to $C_8$ and to the 11-oxy function, if present. (In accordance with accepted convention, an α-substituent at the 8-, 9-, 11- or 12-positions is behind the place of the paper whereas a β-substituent at these positions is in front of the plane of the paper. This is usually represented by a---bond for an α-substituent, a—bond for a β-substituent, and a∿bond where both possibilities are indicated.)

FLOWSHEET D

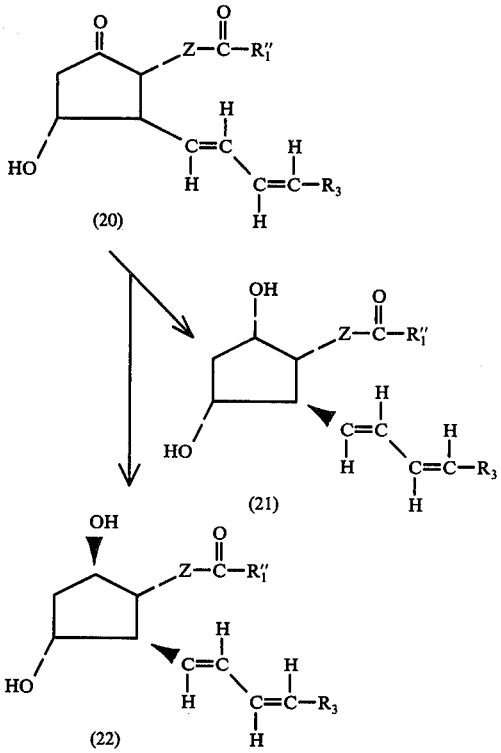

The prostanoic and prostenoic carboxylic acids of this invention are convertible to the corresponding alkyl esters by treatment with the appropriate diazoalkane in the usual manner. The preparation of diazoalkanes by various procedures are well-described in the art, see for example C. D. Gutsche, *Organic Reactions*, VIII, 389 (1954). Certain of the esters of this invention can also be obtained by use of the appropriate cyclopentenone ester (16). The various esters can also be prepared by any of several procedures well-known in the art via an acid chloride (prior blocking of free alcohol groups with appropriate blocking groups such as trialkylsilyl, tetrahydropyranyl, ketals, acetals and the like) or mixed anhydrides and treatment of these intermediates with the appropriate alcohol. Mixed anhydrides can be obtained by treatment of the prostaglandin acid in a solvent such as dioxane at a temperature in the range of 0° to 15° C. with a molar equivalent of a tri-alkylamine, preferably triethylamine, tributylamine and the like, and then a molar equivalent of isobutyl chlorocarbonate or the like. The resulting mixed anhydride is then treated with the appropriate alcohol to give the derivatized product.

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to 1 hour the product is worked-up in the usual manner. (For a pertinent literature analogy see U.S. Pat. No. 3,821,279, June 28, 1974).

The esterified alcohol derivatives ($R_2$ and/or R is alkanoyloxy and/or $R_4$ is alkanoyl) are also prepared in the usual manner by procedures well-known in the art from the appropriate alkanoic acid anhydride or acid chloride.

Also embraced by the present invention are the intermediates expressed by the following generic formulae (23-28) which include both the threo and erythro configurations.

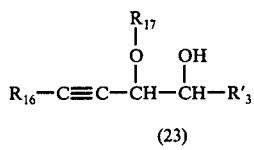

(23)

wherein $R_{16}$ is hydrogen or tri-lower alkylsilyl; $R_{17}$ is hydrogen or tetrahydropyranyl; and $R'_3$ is a straight or branched chain alkenyl group ($C_3$ to $C_6$);

$$J-W_4-R_3 \quad (24)$$

wherein $R_3$ is hereinabove defined; J is selected from the group consisting of:

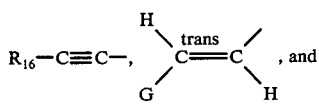

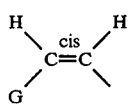

wherein $R_{16}$ is as hereinabove defined and G is a member of the group consisting of iodine, bromine, or lithium atoms and $W_4$ is a divalent radical selected from the group consisting of

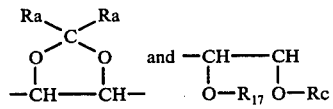

wherein Ra, and Rc are as hereinabove defined and $R_{17}$ is tetrahydropyranyl or trimethylsilyl;

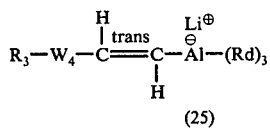

(25)

wherein $R_3$, $W_4$ and $R_d$ are as hereinabove defined;

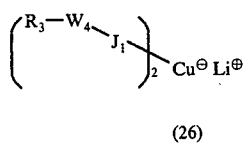

(26)

wherein $R_3$ and $W_4$ are as hereinabove defined and $J_1$, is cis- or trans-vinylene; and the complexes of (65) with trialkyl (3 to 7 carbon atoms, inclusive) phosphines and the like;

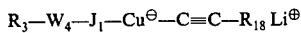

(27)

wherein $R_3$, $W_4$ and J are as hereinabove defined; $R_{18}$ is an alkyl group of from 2 to 5 carbon atoms, inclusive and the complexes of (66) with trialkyl (3 to 7 carbon atoms, inclusive) phosphines or hexa-lower alkylphosphoramides and the like;

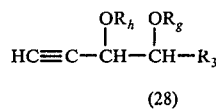

(28)

wherein $R_3$ is as hereinabove defined; Rg is lower alkyl of 1 to 3 carbon atoms, inclusive, lower alkenayl of from 2 to 4 carbon atoms, inclusive; and Rh is hydrogen, arylsulfonyl, lower alkyl sulfonyl, formyl or lower alkanoyl of from 2 to 4 carbon atoms, inclusive.

In Flowsheet B hereinabove, the β-chain precursor (10) and the 4-oxycyclopentenone (16) are in the racemic form, then product (18) will be obtained as a mixture of two racemates. If either the 4-oxycyclopentenone (16, $R'_2$ = oxy group) or the β-chain precursor (10) are in an optically active form two diastereomers result. Separation of racemic or diastereomeric (18) into the component 15-natural and 15-epi racemates or diastereomers in appropriate instances can be accomplished by careful application of the usual chromatographic procedures. In the more difficult instances it may be necessary to apply high pressure liquid chromatography including recycling techniques. [See G. Fallick, *American Laboratory*, 19–27 (August, 1973) as well as references cited therein. Additional information concerning high speed liquid chromatography and the instruments necessary for its application is available from Waters Associate, Inc., Maple St., Milford, Mass.]

The 4-hydroxycyclopentenone racemates may be resolved into their component enantiomers (29) and (30) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride (to give 31), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (29) and (30). A useful procedure for the resolution of a 4-hydroxycyclopentenone racemate via an oxime such as (31) as described in the art [R. Pappo, P. Collins and C. Jung, *Tetrahedron Letters*, 943 (1973)].

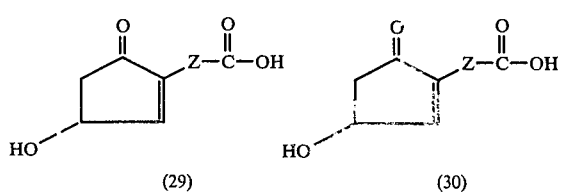

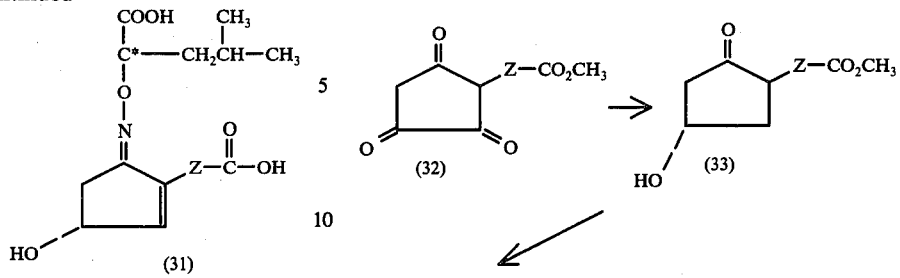

An alternative procedure for the preparation of the 4(R)-hydroxycyclopentenone enantiomers such as (29) involves as a key step the selective microbiological or chemical reduction of trione (32) to the 4(R)-hydroxycyclopentanedione (33). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis(o-anisylcyclohexylmethylphosphine)rhodium (I) tetrafluoroborate in the presence of one equivalent of organic base, such as triethylamine.

Conversion of hydroxycyclopentanedione (33) to an enol ether or enol ester, (34, E = alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° to −15° C. Reduction of (34) with excess sodium bis(2-methoxyethoxy) aluminum hydride in a solvent such as tetrahydrofuran or toluene at low temperatures, such as −60° to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (35). The ester (35) after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih et al., *Journ. Amer. Chem. Soc.*, 95 1676 (1973); 97, 865 (1975); J. B. Heather et al., *Tetrahedron Letters*, 2213 (1973); R. Pappo and P. W. Collins, *Tetrahedron Letters*, 2627 (1972) and R. Pappo, P. Collins and C. Jung, *Ann. N.Y. Acad. Sci.*, 180, 64 (1971). For a descriptive of the baker's yeast procedure see C. J. Sih et al., *Journ. Amer. Chem. Soc.*, 94, 3643 (1972); 97, 857 (1975).

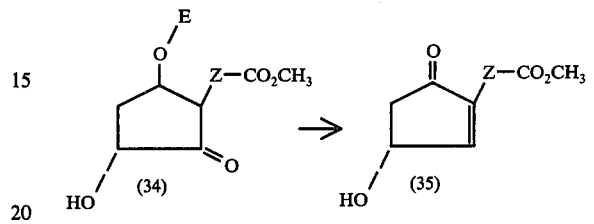

Procedures for the preparation of the requisite cyclopentanetriones (32) are well-established in the art and generally involve the treatment of an ω-1 oxo long chain ester (36) with methyl or ethyl oxalate and a base such as sodium methoxide in methanol, followed by treatment with dilute hydrochloric acid in aqueous methanol to effect the dealkoxalylation of the intermediate (37). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N.Y. Acad. Sci.* 180, 64(1971); C. J. Sih et al., *Journ. Amer. Chem. Soc.*, 95, 1676 (1973) (see reference 7); 87, 865 (1975); and J. B. Heather et al., *Tetrahedron Letters*, 2313 (1973) for pertinent background literature.

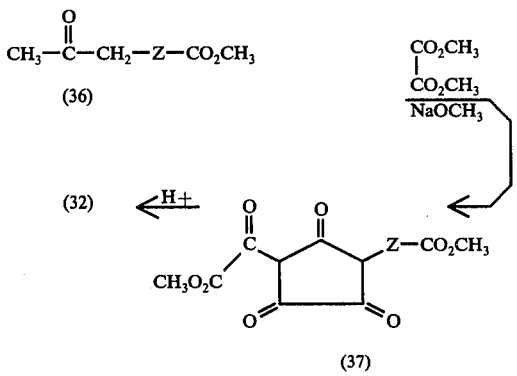

The inermediate keto esters (36) may be prepared by a variety of methods known to the art. One useful procedure is outlined below and invlves alkylation of ethyl acetoacetate sodium salt (38) in the usual manner with the appropriate side-chain precursor (39, X=Cl, Br, I, preferably Br or I) followed by decarbethoxylation and reesterification, all in the usual manner.

(38) + (39)

↓

(41) → (40)

↓

(36)

The side-chain precursors (39) are commercially available where Z is —$(CH_2)_m$—.

It is also possible to resolve the 4-hydroxycyclopentenone racemate (42) by microbiological means. Thus, treatment of the 4-O-alkanoyl or aroyl derivatives (43, $R_{18}$ = aryl or alkyl) of racemate (41) preferably the 4-O-acetyl and 4-O-propionyl derivatives) with an appropriate microorganism, preferably a Saccharomyces species e.g., 1375-143, affords preferential de-O-acylation of the 4(R)-enantiomer to give (44), which is then separated from the unreacted 4(S)-O-acyl enantiomer (45) by chromatographic procedures. After separation, mild hydrolysis of the 4(S) derivatives (45) provides the 4(S)-hydroxycyclopentenone (46). [See N. J. Marscheck and M. Miyano, *Biochimica et Biophysica Acta*, 316, 363 (1973) for related examples.]

(42) → (43) → (44) + (45) → (46)

It is also possible to prepare the individual 4-hydroxycyclopentenones (29) and (30) directly by selective microbial hydroxylations of the corresponding 4-unsubstituted cyclopentenone (47). For example, with *Aspergillus niger* ATCC 9142; a selective 4(R)-hydroxylation of (47, Z = $(CH_2)_6$) has been reported; see S. Kurozumi, T. Tora and S. Ishimoto, *Tetrahedron Letters*, 4959 (1973). Other microorganisms can also accomplish this hydroxylation.

(47)

An alternate resolution procedure involves derivatization of the alcohol function of the racemic hydroxycyclopentenone to give ester-acid derivatives such as (48) wherein R"$_1$ is hydroxy or an alkoxy group, $n'$ is zero or two and Z is as hereinabove defined.

(48)

Such derivatives may be obtained from the corresponding free hydroxycyclopentenone by treatment in the usual manner with oxalyl chloride, succinyl chloride, succinic anhydride and the like. Treatment of the resulting acid or diacid (48), R"$_1$ = hydroxy) with optically active amines e.g., 1-(−)-α-methylbenzylamine, d-(+)-α-methylbenzylamine, brucine, dehydroabietylamine, strychnine, quinine, cinchonine, qunidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(R)- and 4(S)-hydroxycyclopentenone enantiomers (29) and (30) or their respective esters. Cleavage of the oxalate acid ester (48, $n'$ =

0) can be accomplished by treatment with lead tetraacetate in pyridine solution. For an example of a similar use of oxalate acid-esters see J. G. Molotkovsky and L. D. Bergelson, *Tetrahedron Letters,* 4791 (No. 50, 1971); for an example of the use of a succinate acid-ester see B. Goffinet, Ger. Offen. 2,263,880; *Chem. Abstracts,* 79, 78215z (1973).

Appropriate and useful intermediates for the resolution of the racemic β-chain processors are illustrated in Flowsheet A hereinabove.

The racemic β-chain precursors at either the acetylenic alcohol stage or the trans-vinyl iodide state by a variety of methods well-known in the art. These methods will be illustrated below with the acetylenic alcohol (49) wherein R₃ is as hereinabove defined and B is a lower alkanoyloxy or lower alkoxy group, but they apply equally well to the trans-vinyl iodide (50). Furthermore, the resolved acetylenic alcohols corresponding to (49) can be converted to the trans-vinyl iodides corresponding to (50) or its derivatives as described hereinabove without racemixation [see for an example, A. F. Kluge, K. G. Untch and J. H. Fried, *Journ. Amer. Chem. Soc.,* 94, 7827 (1972)].

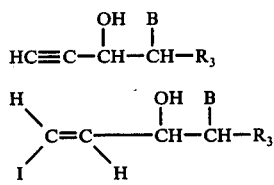

Racemates (49) and (50) could be resolved by reverse phase and absorption chromatography on an optically active support systme or by selective transformation of one isomer by microbiological or enzymatic procedures.

A more generally applicable procedure involves conversion of the racemic alcohol to a mixture of diastereomers by derivatization of the hydroxy function with an optically active reagent, followed by separation of the diastereomers by fractional crystallization or chroamtographic procedures, as discussed hereinabove. Regeneration of the alcohol function from the individual diastereomer would then profide the individual enantiomeric alcohols (51) and (52), shown in the erythro form, but the same applies to the threo derivatives.

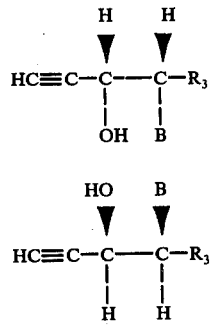

Useful derivatives for resolution purposes include the salts of the phthalate half acid ester (53) with an optically active amine (e.g., 1-(−)-α-methylbenzylamine, d(+)-α-methylbenzylamine, brudine, dehydroabietylamine, strychnine, quinine, cinchonine, cinchonidine, quinidine, ephedrine, deoxyephedrine, amphetamine, (+)-2-amino-1-butanol, (−)-2-amino-1-butanol and the like).

For the resolution in the art of the related 3hydroxy-1-octyne by this procedure see J. Fried et al., *Annals of the N.Y. Acad. of Sci.,* 180, 38 (1971), and of the related 1-iodo-trans-1-octen-3-ol see A. F. Kluge, K. G. Untch and J. H. Fried, *Journ. Amer. Chem. Soc.,* 94, 7827 (1972).

Other useful derivatives would be the diastereomeric carbamates (54) obtained by treatment of racemate (49) with an optically active isocyanate (e.g., (+)-1-phenylethylisocyanate and (−)-1-phenylethylisocyanate).

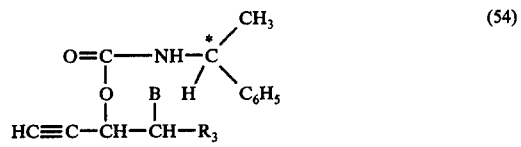

Various esters of racemate (49) with optically active acids could also be useful for resolution purposes. Among the optically active acids which can be used in this connection are -camphoric acid, menthoxyacetic acid, 3α-acetoxy-Δ⁵-etianic acid, 3α-acetoxy-5,16-etiadienoic acid, (−)-α-methoxy-α-trifluoromethylphenylacetic acid (see 51), (+)-α-methoxy-α-trifluoromethylphenylacetic acid, and the like.

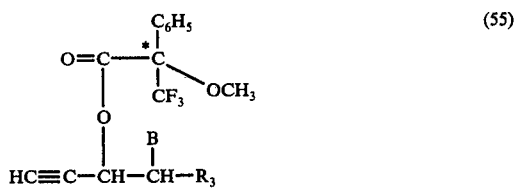

The resolution of the related 1-octyne-3-ol with 3β-acetoxy-Δ⁵-etianic acid and 3β-acetoxy-5,16 -etiadienoic acid has been described in the art [see R. Pappo, P. Collins, and C. Jung, *Annals of the N.Y. Acad. of Sci.,* 180, 64 (1971)].

The ring system of certain of the novel compounds of this invention allow them to be characterized as follows:

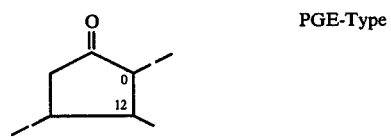
PGE-Type

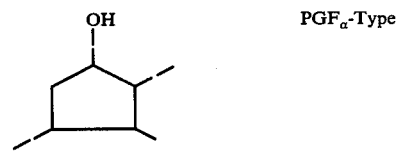
PGFα-Type

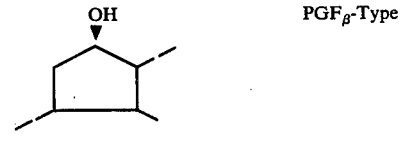
PGFβ-Type

PGA-Type

-continued

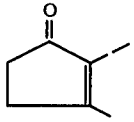
PGB-Type

The novel compounds of this invention possess the pharmacological activity described below as associated with the appropriate above-described prostaglandin type.

The known PGE, PGF$_\alpha$, PGF$_\beta$, PGA, and PGB compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandins analogs is surprisingly and unexpectedly more useful than one of the corresponding above-mentioned known prostaglandins for at least one of the pharmacological purposes indicated below for the latter, either because it has a different and narrower spectrum of biological activity then the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, PGF$\alpha$ and PGF$\beta$ compounds are additionally selective in that they are at most relatively very weak stimulants of smooth muscle. The 11-deoxy PGE compounds have a further advantage in that they are as much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, bucally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body wit fewer, shorter, or smaller doses, and make possible self-administration by the patient.

PEG$_1$, PGE$_2$, PGE$_3$, and dihydro-PEG$_1$, and the corresponding PGF$_\alpha$, PGF$_\beta$, PGA, and PGB compounds, and their esters and and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood pressure lowering in the case of the PGE, and PGF$\beta$ and PGA compounds as measured, for example, in anesthetized (penobarbital sodium) pentolinium-treated rats with indwelling aortic and right heart cannulas; pressor activity, similarly measured, for the PGF$\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the cetral nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds and especially the PGE compounds, are useful in mammals, including man, as nasal decongestants. For this purpose, the compounds are used in a dose range of about 10 μg. to about 10 mg. per ml. of a pharamcologically suitable liquid vehicle or as an aerosol spray, both for topical application.

The PGE and PGA compounds ae useful in mammals, including man and certain useful antimals, e.g., dogs and pigs, to reduce and control excessive gastric secretion, thereby reducing or avoiding gastric erosin or gastrointestinal ulcer formation, and accelerating the healing of such ulcers already present in the gastrointestinal tract. For this purpose, the compounds are injected or infused intravenously, subcutaneously, or intramuscularly in an infusion does range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE$_1$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg. per kg. of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example, to relieve the symptoms of paralytic ileus, or to control or prevent uterine bleeding after abortion or delivery, to aid in explusion of the placenta, and during the puerperium. For the latter purpose, the PGE compound is administered by intravenous infusion immediately after abortion or delvery at a dose in the range about 0.01 to about 50 μg. per kg. of body weight per minute until the desired effect is obtained. Subsequent doses are given by intravenous, subcutaneous, or intramuscular injection or infusion during puerperium in the range of 0.01 to 2 mg. per kg. of body weight per day, the exact dose depending on the age, weight, and condition of the patient or animal.

The PGE, PGFβ and PGA compounds are useful as hypotensive agents to reduce blood pressure in mammals including man. For this purpose, the compounds are administered by intravenous infusion at the rate about 0.01 to about 50 μg. per kg. of body weight per minute, or in a single or multiple doses of about 25 to 2500 μg. per kg. of body weight total per day.

The PGE, PGFα, and PGFβ compounds are useful in place of oxytoxin to induce labor in pregnant female animals, including man, cows, sheep, pigs, at or near term or in pregnant animals with intrauterine death of the fetus from about 20 weeks to term. For this purpose, the compound is infused intravenously at a dose 0.01 to 50 μg. per kg. of body weight per minute until or near the termination of the second stage of labor, i.e., expulsion of the fetus. These compounds are especially useful when the female is 1 or more weeks postmature and natural labor has not started, or 12 to 60 hours after the membranes have ruptured and natural labor has not yet started.

The PGE, PGFα, and PGFβ compounds are useful for controlling the reproductive cycle in ovulating female mammals, includng humans and other animals. For that purpose, $PGF_{2α}$, for example, is administered systematically at a dose level in the range of 0.01 mg. to about 20 mg. per kg. of body weight, advantageously during a span of time starting approximately at the time of ovulation and ending approximately at the time of menses or just prior to menses. Additionally, expulsition of an embryo or fetus is accomplished by similar administration of the compound during the first third or the second third of the normal mammalian gestation period. Accordingly they are useful as abortifacients. They are also useful for induction of menses during apprimately the first 2 weeks of a missed mestrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managin cases of renal disfunction, especially in cases of several impaired renal blood flow, for example, the hepatorena syndrome and early kidney transplant rejection. In case of excessive or inappropriate ADH (antidiuretic hormone vasopressin) secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intraveneous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel compounds of this invention induce the biological responses described hereinabove as associated with its particular prostaglandins type. These novel compounds are accordingly useful for the above-described corresponding purposes in the same manner as described above.

The novel PGE, PGFβ and PGA compounds of this invention are also useful as bronchodilators for the treatment of asthma and chronic bronchitis; as such they may be conveniently administered by inhalation of aerosol sprays prepared in a dose range of about 10 μg. to about 10 mg. per ml. of a pharmacologically suitable liquid vehicle.

In addition certain of the novel compounds of this invention are useful for the preparation of other novel compounds of this invention.

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung,* 18, 955 (1968).]

The compounds of this invention are also useful as inhibitors of gastric acid secretion and peptic ulcer formation and may be used for the treatment of gastric hyperacidity, gastric erosion, and peptic ulcer. Inhibition of basal gastric acid secretion can be determined by the following procedure.

Female Sprague-Dawley rats weighting 140–160 grams are fasted in individual cages for 18–24 hours. The rats are then lightly anesthetized with ether and their front teeth extracted to avoid destruction of the plastic cannula. A midline incision is then made and the stomach and duodenum exposed. A flanged polyvinyl tube is inserted into the fundic portion of the stomach and secured with a purse string suture line using 4–O Mersilene. The rat is then dosed by injection of the compound into the duodenum (1.0 ml. per 100 gram body weight). After dosing, the abdominal wall and skin are closed using metal wound clips. The rat is replaced in a cage containing a longitudinal slit to allow the polyvinyl tube to hang freely. An 8 ml. plastic collecting tube is attached to the flanged cannula and hangs freely below the cage. The first 30 minute sample is discarded designating this time as zero. The collecting tube is attached again and samples removed at the end of 60 and 120 minutes. The hourly samples are then transferred to a 15 ml. centrifuge and centrifuged for 5–10 minutes. Total and sediment volume are then recorded with the supernatant volume being used as volume of secretion. A 1 ml. or less aliquot is then removed and placed in a 50 ml. beaker containing 10 ml. of distilled water. This sample is then titrated using 0.01N NaOH to pH 7.0 using a Beckman zeromatic pH meter. Volume, titratable acidity (meq/L) and total acid output (ueg/hour) are recorded. Percent inhibition is determined by comparison with the appropriate control. Groups of three rats were used for preliminary testing, and groups of six rats were used for dose-response evalutions. All compounds are administered in a vehicle consisting of 0.5% methocel, 0.4% tween 80, and saline at a constant volume of 1 ml./100 gram rat. Samples are dispersed by sonification. Percent inhibition is calculated on basis of concurrent vehicle control.

In Table B which follows is given the effect on total acid output after 60 minutes (response A) and 120 minutes (response B) for various doses of representative compounds of this invention.

The compounds of the present invention exhibit hypotensive activity when tested in the following procedure:

The animals used are Royalhart, Wistar strain, male, normotensive rats weighing 250–300 g. The rats are anesthetized using a 100 mg./ml. saline solution of urethane at a rate of 900 mg./kg. intraperitoneally.

The instrumentation used in a Brush model 260 recorder, Statham mode P23Db pressure transducer and Harvard model 940 infusion pump with a 6 cc syringe at speed 4.

The left carotid artery is cannulated with polyethylene tubing for arterial blood pressure. The left external juglar vein is cannulated with polyethylene tubing for bration period the test compound is infused over a 1 minute period in a volume of 0.5 ml., at a concentration of 2.5 mg./kg. in one of three diluents (ethanol, 1M $NaHCO_3$ or saline) and then flushed with 0.4 ml. of saline.

This invention will be described in greater detail in conjunction with the following specific examples.

EXAMPLE 1

Preparation of 3-tetrahydropyranyloxy-1-propyne

To a stirred solution of 112 g. (2.0 mol.) of 3-hydroxy-1-propyne and 260 g. (3.0 mol.), of dihydropyran in 1.20 l. of methylene chloride cooled to 0° C. in an ice bath, is added a solution of 20 mg. of para-toluenesulfonic acid in 100 ml. of methylene chloride, dropwise. The reaction mixture is stirred at 0° C. for one-half hour, and at ambient temperature for 1 hour. It is then poured into 200 ml. of a 5% solution of sodium bicarbonate, the organic phase is separated, the aqueous phase extracted with 100 ml. of methylene chloride, the combined organic phases washed with 100 ml. of a solution of brine, dried over sodium sulfate, and evaporated under vacuum (12 mm.) at 45° C., to give 300 g. of crude product, which is purified by fractional distillation, b,p, 71°–73° C. (14 mm.) to yield 250 g. (89%) of a liquid.

EXAMPLE 2

Preparation of 3-tetrahydropyranyloxy-1-trimethylsilyl-1-propyne

To a stirred −20° C. solution of 125 g. (0.89 mol.) of 3-tetrahydropyranyloxy-1-propyne (Example 1) in 450 ml. of ether, under a nitrogen atmosphere, is added dropwise, over one hour, a solution of 45 ml. (0.89 mol.) of 2.0 N n-butyllithium in hexane. After 150 ml. of dry ether is added and the mixture stirred at −20° C. for 30 minutes, a solution of 98 g. (0.89 mol.) of trimethylchlorosilane in 73 ml. of ether is added dropwise, stirring is continued for 30 minutes at −20° C., and at ambient temperature for 18 hours. The reaction mixture is again cooled to −20° C., and a solution of 90 ml. of acetic acid in 300 ml. of ether is added dropwise, followed by 90 ml. of water. It is then diluted with 500 ml. of water, and extracted 3 times with 300 ml. of a 5% sodium bicarbonate solution. The organic phase is separated, washed with 500 ml. of a saturated brine solution, dried over sodium sulfate, and evaporated at 40° C. under vacuum (12 mm.). The crude product is fractionally distilled, b.p. 120°–125° C. (18 mm.), to yield 120 g. of an oil.

EXAMPLE 3

Preparation of d,l-erythro-3-tetrahydropyranyloxy-4-hydroxy-1-trimethylsilyl-1-octyne To a stirred −78° C. solution of 62 ml. (124 mmol.) of a 2.0 M solution of n-butyllithium in hexane and 50 ml. of dry tetrahydrofuran, under a nitrogen atmosphere is added dropwise a solution of 24 g. (113 mmol.) of 3-tetrahydropyranyloxy-1-trimethylsilyl-1-propyne (Example 2) in 35 ml. of tetrahydrofuran. This red solution is stirred 1 hour at −78° C. then a freshly prepared solution of zinc iodide (135 mmol.) in 125 ml. of tetrahydrofuran [F. Mercier, R. Epsztein, and S. Holand, *Bull. Soc. Chim. France*, 2, 690, (1972)] is added dropwise at −78° C. until the mixture turns yellow. After stirring an additional hour at −78° C., a solution of 21 g. (250 mmol.) of n-valeraldehyde in 35 ml. of tetrahydrofuran is added dropwise and the reaction mixture stirred for 1 hour at −78° C. and 18 hours at ambient temperature. It is then cooled to 0° C. and a solution of 12 ml. of acetic acid in 65 ml. of ether is added dropwise, followed by 75 ml. of ice-water. The phases are separated and the aqueous phase is extracted twice with ether. The combined organic phases are washed 3 times with saturated sodium bicarboante solution, until the last wash is basic, then with a saturated brine solution, dried over sodium sulfate, and evaporated to give 40 g. of a yellow oil. The crude product may be purified on a 4 × 40 inch dry column of alumina, and eluted with chloroform. I.R.: neat; 3550 (OH), 2200 (C≡C), 840, 750 [(CH$_3$)$_3$Si], cm$^{-1}$.

EXAMPLE 4

Preparation of d,l-erythro-3,4-dihydroxy-1-trimethylsilyl-1-octyne

A solution of 19.6 g. (.066 mol.) of d,l-erythro-3-tetrahydropyranyloxy-4-hydroxy-1-trimethylsilyl-1-octyne (Example 3) in 55.5 ml. of ethanol, 22.2 ml. of acetic acid, and 22.2 ml. of water is heated at reflux for 3 hours. The cooled mixture is taken to dryness and evaporated twice with benzene. The residue is taken up in hexane, washed 3 times with saturated potassium bicarbonate solution, dryed with magnesium sulfate, and evaporated to give 17.0 g. of crude product.

IR: neat, 3500–3400, broad (two OH).

EXAMPLE 5

Preparation of d,l-erythro-3,4-isopropylidenedioxy-1-trimethylsilyl-1-octyne

To a stirred solution of 17.0 g. (79.5 mmol.) of crude d,l-erythro-15,16-dihydroxy-1-trimethylsilyl-1-octyne (Example 4) in 33.6 ml. of 2,2-dimethoxy propane at 0° C., is added 0.05 ml. of 60% perchloric acid. After 30 minutes at ambient temperature, the mixture is shaken with 50 ml. of hexane and 25 ml. of saturated sodium bicarbonate solution. The hexane phase is separated, dryed with magnesium sulfate, and evaporated to give 19.0 g. of crude product.

EXAMPLE 6

Preparation of d,l-erythro-3,4-isopropylidenedioxy-1-octyne

A mixture of 19.0 g. (75.0 mmol.) of crude d,l-erythro-3,4-isopropylidenedioxy-1-trimethylsilyl-1-octyne (Example 5) with 95 ml. of methanol and 3.0 g. of potassium carbonate is refluxed for 1 hour. The mixture is cooled and evaporated at 50° C. (13 mm.), taken up in 250 ml. of benzene, and washed with 100 ml. of water. The water is saturated with salt, the organic phase separated, dried with mangesium sulfate, and evaporated to give 12 g. of crude product. Fractional distillation yields 7.0 g. of the subject compound as a colorless oil, b.p. 103°–106° C. (13 mm.).

IR: neat; 3300 sharp (H—C≡C), 2100, (C≡C), 780 (erythro configuration) cm$^{-1}$.

nmr: $\delta_{TMS}^{CDCl_3}$; 4.75 (dd., 1, C≡C—C$\underline{H}$—CH, J=2Hz, J=5Hz), 4.10 (m, 1, C≡C—CH—C$\underline{H}$—CH$_2$, 2.5 (d, 1, $\underline{H}$—C≡C—CH), 1.9–1.2 (m, 14, alkyl), .90 (m, 3H, CH$_2$C$\underline{H}_3$).

EXAMPLE 7

Preparation of d,l-erythro-1-iodo-3,4-isopropylidenedioxy-trans-1-octene

To a stirred 0° C. slurry of 0.852 g. (.023 mol.) of sodium borohydride and 4.21 g. (.060 mol.) of 2-methyl-2-butene in 40 ml. of dry tetrahydrofuran, under an argon atmosphere, is added dropwise 4.26 g. (.030 mol.) of boron trifluoride etherate complex. A solution of 2.73 g. (.015 mol.) of d,l-erythro-3,4-isopropylidenedioxy-1-octyne (Example 6) in 5 ml. of tetrahydrofuran in added dropwise, the ice bath removed, and the mixture allowed to stir at ambient temperature for 2 hours. It is then cooled again to 0° C., and 2.88 g. (0.105 mol.) of dry trimethylamine oxide is added in portions over 30 minutes. After stirring 3 hours at room temperature, this mixture is poured simultaneously with a 0° C. solution of 21.3 g. of iodine in 53 ml. of tetrahydrofuran into 766 ml. of a 0° C. 15% solution of sodium hydroxide in water and the whole stirred vigorously at 0° C. for 45 minutes. The organic phase is separated, the aqueous phase is extracted twice with ether, the combined organic phases are washed with a 5% solution of sodium thiosulfate, dried with magnesium sulfate, and evaporated. The crude product is chromatographed on a 2 × 40 inch dry column of silica gel, by eluting with chloroform, to yield 1.2 g. (25%) of a yellow oil.

IR: neat; 1599 sharp, 945

cm$^{-1}$.

EXAMPLE 8

Preparation of d,l-erythro-9-oxo-11α-tetrahydropyranyloxy-15,16-isopropylidenedioxy-5-cis,13-trans-prostadienoic acid In the manner of Example 20, conjugate addition of 4.96 g. (16.0 mmol.) of d,l-erythro-1-iodo-3,4-isopropylidenedioxy-trans-1-octene to 5.35 g. (16.0 mmol) of 2-(6-carbotetrahydropyranyloxy-2-cis-hexenyl)-4-tetrahydropyranyloxycyclopent-2-en-1-one (U.S. Pat. No. 3,873,607; Mar. 25, 1975) is followed by the same workup procedure as in Example 18. The mixture obtained is then stirred at 25° C. for 1 hour in 500 ml. of a solution of 100 ml. of acetic acid to 100 ml. of tetrahydrofuran and 40 ml. of water. An equal volume of water is then added and the mixture is extracted 3 times with ether, washed with a solution of brine, and dried over mangesium sulfate to give a yellow oil containing the product. This is chromatographed on a 3 × 40 inch dry column of silica gel, and eluted with a solution of 0.5% acetic acid in ether to yield 1.10 g. (14 percent) of chromatographically pure product, which is a 15-epimeric mixture.

IR: neat, 3550 (COOH), 1740, 1700 (C=O), 970

cm$^{-1}$.

EXAMPLE 9

Preparation of d,l-erythro-9-oxo-11α-hydroxy-15,16-isopropylidenedioxy-5-cis,13-trans-prostadienoic acid and d,l-erythro-9-oxo-11α-hydroxy-15-epi,16-isopropylidenedioxy-5-cis,13-trans-prostadienoic acid A solution of 492 mg. (1mmol.) of d,l-erythro-9-oxo-11α-tetrahydropyranyloxy-15,16-isopropylidenedioxy-5-cis,13-trans-prostadienoic acid (Example 26) in 20 ml. of acetic acid, 10 ml. of tetrahydrofuran and 5 ml. of water is stirred and heated at 45° C. for 2.5 hours. Using high vacuum at 45° C. the solution is taken to dryness and evaporated twice with benzene to give an oil containing the subject product and other products of the deblocking, as in Example 26. The subject epimeric products are obtained by chromatography on a 2 × 40 inch dry column of silica gel and eluted with a solution of 0.5% acetic acid in ether.

EXAMPLE 10

Preparation of d,l-erythro-9-oxo-11α,15,16-trihydroxy-5-cis,13-trans-prostadienoic acid and d,l-erythro-9-oxo-11α,15-epi,16-trihydroxy-5-cis,13-trans-prostadienoic acid In the manner of Example 27, treatment of d,l-erythro-9-oxo-11α-tetrahydropyranyloxy-15,16-isopropylidenedioxy-5-cis,13-trans-prostadienoic acid (Example 26) with acetic acid, tetrahydrofuran, and water at 55° C. for 8 hours, and subsequent dry column chromatography is productive of the subject compounds.

nmr: $\delta_{TMS}^{CDCl_3}$; 6.5–5.2 (bm., 8,

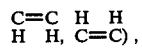

4OH, 4.5–3.5 (bm., 3, OCH), 2.8–1.1 (bm, 18, alkyl), 0.9 (m, 3, CH$_2$C$\underline{H}_3$).

EXAMPLE 11

Preparation of 2-(6-carbotrimethylsilyloxy-2-cis-hexenyl)-4-trimethylsilyloxy-cyclopent-2-en-1-one To a stirred solution of 25.28 g. (0.114 mol.) of 2-(6-carboxy-2-cis-hexenyl)-4α-hydroxy-cyclopent-2-en-1-one [(M. B. Floyd, Synthetic Communications, 4, 317 (1974)] and 42.06 g. (0.392 mol.) of trimethylchlorosilane in 50 ml. of dry dimethylformamide, under a nitrogen atmosphere, cooled in an ice bath, is added dropwise 25.28 g. (0.250 mol.) of triethylamine. The mixture is next stirred and heated at 65° C. for 4 hours and at room temperature for 15 hours. It is then cooled, filtered, and the solvent removed under high vacuum (1.0 mm.) at 40° C. The residue is dissolved in one liter of hexane, activated charcoal added, and filtered through a pad of florisil and celite. In the same manner, the solution is again clarified, evaporated under vacuum and dried under high vacuum at room temperature for 15 hours to give 25.13 g. of ano oil.

EXAMPLE 12

Preparation of d,l-erythro-1-iodo-3,4-dihydroxy-trans-1-octene

A solution of 1.40 g. (4.50 mmol.) of d,l-erythro-1-iodo-3,4-isopropylidenedioxy-trans-1-octene (Example 7) in 30 ml. of acetic acid, 10 ml. of tetrahydrofuran and 10 ml. of water is stirred and heated at 50° C. for 5 hours. It is then evaporated at 40° C. under high vacuum (1.0 mm.), and twice more with 50 ml. of benzene. Crystallization from 10 ml. of chloroform at 0° C. is productive of 700 mg. of the white crystalline subject product.

EXAMPLE 13

Preparation of d,l-erythro-1-iodo-3,4-bis-trimethylsilyloxy-trans-1-octene

To a stirred solution of 700 mg. (2.40 mmol.) of d,l-erythro-1-iodo-3,4-dihydroxy-trans-1-octene (Example 32) and 800 mg. (12.0 mmol.) of imidazole, in 10 ml. of dry dimethylformamide at 0° C. is added dropwise 1.20 g. (11.0 mmol.) of trimethylchlorosilane. The ice bath is removed, and the mixture is stirred and heated at 50° C. for 5 hours. It is then cooled, shaken with 50 ml. of hexane and 50 ml. of water, the organic layer separated and washed with 15 ml. of 0.5M hydrochloric acid, 15 ml. of a saturated solution of sodium bicarbonate, dried with magnesium sulfate, and evaporated. This crude product is fractionally distilled, b.p. 90°–92° C. (0.40 mm.) to yield 250 mg. of a colorless oil.

EXAMPLE 14

Alternate preparation of d,l-erythro-9-oxo-11, 15,16-trihydroxy-5-cis,13-trans-prostadienoic acid and its 15-epimer To a stirred solution of 473 mg. (1.14 mmol.) of d,l-erythro-1-iodo-3,4-bis-trimethylsilyloxy-trans-1-octene (Example 13) in 6.0 ml. of dry ether at −78° C. under argon, is added 2.90 ml. of a 0.80 M solution of t-butyl lithium (2.40 mmol.) and stirring at −78° C. is continued for 2 hours. A solution of 123 mg. (1.14 mmol.) of thiophenol in 3.0 ml. of ether, under an argon atmosphere, is then treated with 0.50 ml. (1.14 mmol.) of a 2.30 M solution of n-butyllithium in pentane, by dropwise addition at 0° C., and the mixture is stirred for 15 minutes. Then a solution of 450 mg. (1.14 mmol.) of tri-n-butylphosphine copper (I)-iodide complex in 6.0 ml. of ether is added dropwise to the lithium thiophenoxide solution at −78° C. The resulting mixture is stirred a further 15 minutes, added slowly to the vinyllithium solution, and the whole is stirred for 45 minutes at −78° C. A solution of 420 mg. (1.14 mmol.) of 2-(6-carbotrimethylsilyloxy-2-cis-hexenyl)-4-trimethylsilyloxy-cyclopent 2-en-1-one (Example 11) in 5.0 ml. of ether is next added and stirring continued at −40° C. for 2 hours. The reaction is quenched at −40° C. with 135 mg. (2.28 mmol.) of acetic acid in 2.0 ml. of ether, poured into 30 ml. of a saturated ammonium chloride solution, extracted three times with 50 ml. of ether, the combined organic phases washed with 30 ml. of ammonium chloride solution, dried with magnesium sulfate, and evaporated under vacuum. The residue is stirred with a mixture of 15 ml. of acetic acid, 5 ml. of tetrahydrofuran, and 5 ml. of water for one hour at ambient temperature, taken to dryness and evaporated three times with 50 ml. of toluene at 50° C. (1.0 mm.) to remove thiophenol. The purified epimeric subject products are obtained by chromatography of the resulting oil following the method of Example 9.

EXAMPLE 15

2-trans-n-pentenol provides dl-erythro-1-trimethylsilyl-3-tetrahydropyranyloxy-4-hydroxy-5-trans-en-1-octyne.

EXAMPLE 16

Preparation of
d,l-erythro-1-iodo-3,4-isopropylidenedioxy-trans-1-5-octadiene

Hydrolysis of the 3-tetrahydropyranyloxy group of the d,l-erythro-1-trimethylsilyl-3-tetrahydropyranyloxy-4-hydroxy-5-trans-en-1-octyne by the method described in Example 4, followed by conversion of the resulting d,l-erythro-1-trimethylsilyl-3,4-dihydroxy-1-alkyne to the corresponding d,l-erythro-1-trimethylsilyl-3,4-isopropylidenedioxy-1-alkyne by treatment with dimethoxypropane in the presence of perchloric acid by the method described in Example 5, followed by desilylation to the corresponding d,l-erythro-3,4-isopropylidenedioxy-1-alkyne by the procedure of Example 6, followed by treatment with disiamylborane, trimethylamine oxide, iodine, and sodium hydroxide solution by the method described in Example 7, provides the product d,l-erythro-1-iodo-3,4-isopropylidenedioxy-1-trans-5-octadiene.

EXAMPLES 17-22

Conjugate addition of the 4-tetrahydropyranyloxy-cyclopentenones listed in Table I below with the lithium thiophenoxide cuprate prepared from d,l-erythio-1-iodo-3,4-isopropylidiene by the method of Example 14, provides the corresponding tetrahydropyranyl 9-oxo-11α-tetrahydropyranyloxy-15,16-isopropylidenedioxy-13-trans-17-trans prostadienate. The tetrahydropyranyl ester when treated by the acid hydrolysis conditions of Example 8 gives the 9-oxo-11α-tetrahydropyranyloxy-15,16-isopropylidenedioxy-13-trans-17-trans-prostadienoic acid of the table. The 15-epimeric racemates corresponding to the products listed in Table I below may then be separated by careful chromatography as described in Example 9.

TABLE I

| Ex. | Starting 4-tetrahydropyranyloxy cyclopentenone | Starting 1-iodo-3,4-isopropylidenedioxy-trans-1-alkene of Example | Product 9-oxo-11α-tetrahydropyranyloxy-15,16-isopropylidenedioxy-13-trans-prostenoic acid or ester and its 15-epimer |
|---|---|---|---|
| 17 | 2(-6-carbotetrahydropyranyloxy-hexyl)-4-tetrahydropyranyloxy-cyclopent-2-en-1-one | 16 | d,l-erythro-9-oxo-11α-tetrahydropyranyloxy-15,16-isopropylidenedioxy-13-trans,17-trans-prostadienoic acid |
| 18 | 2-(6-carbomethoxyhexyl)-(4R)-tetrahydropyranyloxy-cyclopent-2-en-1-one | 16 | 1-erythro-methyl-9-oxo-11α-tetrahydropyranyloxy-15,16-isopropylidenedioxy-13-trans,17-trans-prostadienoate |
| 19 | 2-(6-carbomethoxyhexyl)-(4S)-tetrahydropyranyloxy-cyclopent-2-en-1-one | 16 | d-erythro-methyl-9-oxo-11α-tetrahydropyranyloxy-15,16-isopropylidenedioxy-13-trans,17-trans-prostadienoate |
| 20 | 2-(6-carbotetrahydropyranyloxy-2-cis-hexenyl)-4-tetrahydropyranyloxy-cyclopent-2-en-1-one | 16 | d,l-erythro-9-oxo-11α-tetrahydropyranyloxy-15,16-isopropylidenedioxy-5-cis,13-trans,17-trans-prostatrienoic acid |
| 21 | 2-(6-carbomethoxy-2-cis-hexenyl)-(4R)-tetrahydrpyranyloxy-cyclopent-2-en-1-one | 16 | 1-erythro-methyl-9-oxo-11α-tetrahydropyranyloxy-15,16-isopylidenedioxy-5-cis,13-trans,17-trans-prostatrienoate |
| 22 | 2-(6-carbotetrahydropyranyloxy-(4R)-methyl-2-cis-hexenyl)-4-tetrahydropyranyloxy-cyclopent-2-en-1-one | 16 | d,l-erythro-(4R)-methyl-9-oxo-11α-tetrahydropranyloxy-15,16-isopropylidenedioxy-5-cis,13-trans-,17-trans-prostatrienoic acid |

EXAMPLES 23-27

Acid hydrolysis of the individual 9-oxo-11α-tetrahydropyranyloxy-15,16-isopropylidenedioxy-17-trans-prostenoic acids or esters and their 15-epimeric racemates, of Table II using the procedure of Example 9, affords the corresponding 11α-hydroxy-15,16-isopropylidenedioxy-prostenoic acids, which may then be isolated at this stage. If hydroylsis is continued as in Example 10, the fully deblocked 9-oxo-11α,15,16-trihydroxy-prostenoic acid or ester and its 15-epimer of Table II below, is obtained.

TABLE II

| Ex. | Starting 9-oxo-11-tetrahydropyranyloxy-15,16-isopropylidenedioxy-13-trans-prostenoic acid or ester and its 15-epimer of Example | Product 9-oxo-11α-15,16-trihydroxy-13-trans-prostenoic acid or ester and its 15-epimeric racemate |
|---|---|---|
| 23 | 17 | d,l-erythro-9-oxo-11α,15,16-trihydroxy-13-trans,17-trans-prostenoic acid |
| 24 | 18 | 1-erythro-methyl-9-oxo-11α,15,16-trihydroxy-13-trans,17-trans-prostadienoate |
| 25 | 19 | d-erythro-methyl-9-oxo-11α,15,16-trihydroxy-13-trans,17-trans-prostadienoate |
| 26 | 20 | d,l-erythro-9-oxo-11α,15,16-trihydroxy-5-cis,13-trans,17-trans-prostatrienoic acid |
| 27 | 21 | 1-erythro-methyl-9-oxo-11α,15,16-trihydroxy-5-cis,13-trans-17-trans-prostatrienoate |

EXAMPLE 28

Preparation of
dl-erythro-9-oxo-15,16-dihydroxy-5-cis,10,13-trans-prostatrienoic acid and
dl-erythro-9-oxo-15-epi,16-dihydroxy-5-cis,10,13-trans-prostatrienoic acid A solution of 50 mg. (0.142 mmol.) of dl-erthyro-9oxo-11α, 15,16-trihydroxy-5-cis,13-trans-prostatrienoic acid (Example 14) in 1.0 ml. of 1.5N hydrochloric acid and 2.0 ml. of tetrahydrofuran under an argon atmosphere is stirred at ambient temperature for 70 hours. The solution is then diluted with 5.0 ml. of saturated sodium chloride solution, extracted with three 5.0 ml. portions of ether, the combined organic phases dried with magnesium sulfate, and evaporated under vacuum, to give the crude 15-normal product. This is purified on a silica gel glass plate by thin layer chromatography, and eluted with a solution of ethyl acetate containing 1.0% ethanol and 1.0% of acetic acid, to give 40 mg. of the 15-normal subject product as a yellow oil. Treatment of 50 mg. of dl-erythro-9-oxo-11α, 15-epi, 16-trihydroxy-5-cis,13-trans-prostatrienoic acid (Example 14) in the same manner as above, is prosuctive of the 15-epi racemic subject product.

EXAMPLES 29–31

Following the procedure of Example 27, treatment of the 9-oxo-11α, 15,16-trihydroxy-13-trans-prostenoic acids or esters of Table III below with 1.5N hydrochloric acid in tetrahydrofuran for 70 hours is productive of the corresponding product 9-oxo-15,16-dihydroxy-10,13-trans-prostenoic acids or ester of the table.

reduction of dl-erythro-9-oxo-11α,15-epi,16-trihydroxy-5-cis,13-trans-prostadienoic acid (Example 14) with sodium borohydride in ethanol is productive of both dl-erythro-9α and 9β,11,15-epi,16-tetrahydroxy-5-cis,13-trans-prostadienoic acid subject racemates which are also separated according to the above procedure.

EXAMPLES 33–37

In Table IV below, treatment of the listed 9-oxo-11α,15,16-trihydroxy-13-trans-prostenoic acids and esters with sodium borohydride in ethanol, using the procedure of Example 31, with subsequent separation of the 9α and 9β racemates, is productive of the corresponding 9α or 9β-hydroxy-prostenoic acids or esters of the table. Only the 9α-hydroxy racemate example is listed in Table IV. Similar treatment of the corresponding 15-epimeric starting 9-ones of the table gives the corresponding 15-epimeric 9α-ol and 9β-ols.

TABLE IV

| Ex. | Starting 9-oxo-prostenoic acids or esters of Example | Product 9α-hydroxy substituted prostenoic acids or esters and the corresponding 9 -ol |
|---|---|---|
| 33 | 23 | dl-erythro-9α,11α,15,16-tetrahydroxy-13-trans,17-trans-prostadienoic acid |
| 34 | 24 | l-erythro-methyl-9α,11α,15,16-tetrahydroxy-13-trans,17-trans-prostadienoate |
| 35 | 25 | d-erythro-methyl-9α,11α,15,16-tetrahydroxy-13,17-trans-prostadienoate |
| 36 | 26 | dl-erythro-9α,11α-15,16-tetrahydroxy-5-cis,13-trans,17-trans-prostatrienoic acid |
| 37 | 27 | l-erythro-methyl-9α,11α,15,16-tetrahydroxy-5-cis,13-trans,17-trans-prostatrienoate |

EXAMPLE 38

Preparation of dl-erythro-9α,11α,15,16-tetrahydroxy-5-cis,13-trans-prostadienoic acid and its 15-epimer

TABLE III

| Ex. | Starting 9-oxo-11 ,15,16-trihydroxy or 11 ,15-di hydroxy-16-alkoxy-13-trans-prostenoic acids or esters of Example | Product 9-oxo-15,16-dihydroxy- or 15-hydroxy-16-alkoxy-10,13-trans-prostenoic acid or ester |
|---|---|---|
| 29 | 23 | dl-erythro-9-oxo-15,16,-dihydroxy-10,13-trans,17-trans-prostatrienoic acid |
| 29 | 24 | l-erythro-methyl-9-oxo-15,16-dihydroxy-10,13-trans,17-trans-prostatrienoate |
| 31 | 27 | l-erythro-methyl-9-oxo-15,16-dihydroxy-5-cis,10,13-trans,17-trans-prostatetraenoate |

EXAMPLE 32

Preparation of dl-erythro-9α, 11α, 15,16-tetrahydroxy-5-cis,13-trans-prostadienoic acid and dl-erythro-9β, 11β, 15,16-tetrahydroxy-5-cis,13-trans-prostadienoic acid and their 15-epimeric racemates To a solution of 500 mg. (1.35 mmol.) of dl-erythro-9-oxo-11α, 15,16-trihydroxy-5-cis,13-trans-prostadienoic acid (Example 14) in 10.0 ml. of 95% ethanol is added portionwise with stirring 400 mg. (10.6 mmol.) of sodium borohydride. The mixture is stirred for 1 hour, poured into 10 ml. of water acidified with hydrochloric acid, extracted twice with 20 ml. each of ethyl ether, the combined organic layers washed with 5 ml. of a saturated solution of sodium chloride, dryed with magnesium sulfate, filtered, and evaporated under vacuum to give the 9α and 9β-hydroxy subject racemates. These are separated on a 1.0 in. × 36 in. dry column of silica gel and eluted with a solution of 1% ethanol and 1% acetic acid in ethyl acetate affording the separated racemates as viscous colorless oils. In the same manner, To a −20° C. stirred solution of 300 mg. (0.813 mmol) of dl-erytho-9-oxo-11α,15,16-trihydroxy-5-cis,13-trans-prostadienoic acid (Example 14) in 12.0 ml. of dry tetrahydrofuran, under an argon atmosphere is added dropwise 4.40 ml. of a 0.5M solution (2.20 mmol.) of lithium perhydro-9b-boraphenalylhydride in tetrahydrofuran. The mixture is stirred and allowed to warm to −5° C. over a 1 hour period. Then, 0.18 g. of sodium hydroxide in 3.0 ml. of water and 2.0 ml. of a 30% solution of hydrogen peroxide are added and stirring continued for 5 minutes. This mixture is poured into 10 ml. of water, extracted twice with 20 ml. each of ethyl ether, and acidified to pH one with 3.0 N hydrochloric acid. The water solution is saturated with sodium chloride, extracted twice with 25 ml. of ether, the combinated organic phases dried with magnesium sulfate, filtered, and evaporated affording 290 mg. of the subject 9α-hydroxy product, exclusively, as a white viscous oil. It may be purified by crystallization from ethyl ether at −30° C. By the same procedure, reduction of dl-erythro-9-oxo-11α,15-epi,16-trihydroxy-5-cis,13-trans-prostadienoic acid (Example 14) is productive of the corresponding 15-epimeric racemate, dl-erythro-9α,1-1α,15-15-epi,16-tetrahydroxy-5-cis,13-trans-prostadienoic acid.

EXAMPLE 39

Following the method of Example 36, treatment of the 9-oxo-prostenoic ester, listed below, or their 15-epimeric racemates, with lithium perhydro-9b-boraphenalylhydride in tetrahydrofuran is productive of the corresponding 9α-hydroxy-hydroxy prostenoic acids or esters or their 15-epimeric racemates of Table V. This reduction results exclusively in 9α-hydroxy isomers as shown in the table.

TABLE V

| Ex. | Starting 9-oxo-prostenoic acids or esters of their 15-epimeric racemates of Example | Product 9α-hydroxy substituted prostenoic acids or esters or their 15-epimers |
|---|---|---|
| 39 | 24 | l-erythro-methyl-9,11,15,16-tetrahydroxy-13-trans,17-trans-prostadienoate |

EXAMPLE 40

Preparation of dl-erythro-methyl-9-oxo-11α,15,16-trihydroxy-5-cis,13-trans-prostadienoate and dl-erythro-methyl-9-oxo-11α,15-epi,16-trihydroxy-5-cis,13-trans-prostadienoate To a solution of 100 mg. (0.272 mmol of dl-erythro-9-oxo-11α,15,16-trihydroxy-5-cis,13-trans-prostadienoic acid in 2.0 ml. of ethyl ether, at 0° C. in an ice bath, is added dropwise with stirring, a solution of diazomethane in ethyl ether until an excess is added, as indicated by the yellow color of the mixture produced, stirring is continued at 0° C. for 1 hour, excess diazomethane is destroyed by dropwise addition of acetic acid, and the ether solvent is removed by evaporation under vacuum. The product is then evaporated three times with 10 ml. each of benzene to remove traces of acetic acid, under high vacuum at 40° C., to yield the methylated subject compound as a yellow oil. Following the same procedure with the 15-epimeric racemic acid is productive of the dl-erythro-methyl-9-oxo-11α,15-epi,16-trihydroxy-5-cis,13-trans-prostadienoate subject product.

We claim:
1. An optically active compound of the formula:

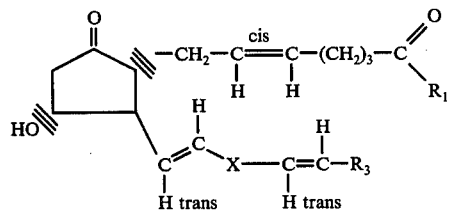

which represents the natural (nat.) configuration or a racemic mixture of that compound and the enantiomer thereof, wherein $R_1$ is hydroxy or $C_1$–$C_5$ alkoxy; $R_3$ is methyl, ethyl or propyl; X is divalent radical

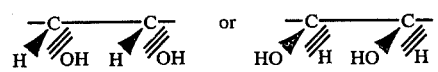

and the pharmacologically acceptable cationic salts thereof when $R_1$ is hydroxy.

2. An optically active compound of the formula:

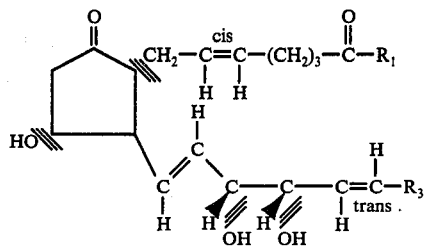

which represents the natural(nat.) configuration or a racemic mixture of the compound and the enantiomer thereof, wherein $R_1$ is hydroxy or $C_1$–$C_5$ alkoxy; $R_3$ is methyl, ethyl or propyl, and the pharmacologically acceptable cationic salts thereof when $R_1$ is hydroxy.

3. An optically active compound of the formula:

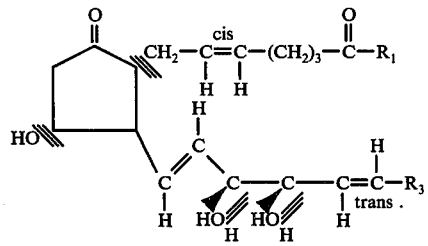

which represents natural(nat.) configuration or a racemic mixture of that compound and the enantiomer thereof, wherein $R_1$ is hydroxy or $C_1$–$C_5$ alkoxy; $R_3$ is methyl, ethyl or propyl; and the pharmacologically acceptable cationic salts thereof when $R_1$ is hydroxy.

4. The compound according to claim 2 dl-erythro-9-oxo-11α,15,16-trihydroxy-5-cis-13-trans-17-trans-prostatrienoic acid.

5. The compound according to claim 2 nat-erythro-methyl-9-oxo-11α,15,16-trihydroxy-5-cis-13-trans-17-trans prostatrienoate.

6. The compound according to claim 3 dl-erythro-9-oxo-11α,15-epi,16-trihydroxy-5-cis-13-trans-17-trans-prostatrienoic acid.

7. The compound according to claim 3 nat-erythro-methyl-9-oxo-11α,15 epi, 16trihydroxy-5-cis-13-trans-17-trans prostatrienoate.

8. The compound according to claim 2 dl-erythro-9-oxo-11α,15,16-trihydroxy-20-methyl-5-cis-13-trans-17-trans prostatrienoic acid.

9. The compound according to claim 2 nat-erythro9-oxo-11α,15,16-trihydroxy-20-methyl-5-cis-13-trans-17-trans prostatrienoic acid.

10. The compound according to claim 2 dl-erythro-methyl 9-oxo-11α,15,16-trihydroxy-20-methyl-5-cis, 13-trans, 17-trans-prostatrienoate.

11. The compound according to claim 2 nat-erythro-methyl-9-oxo-11α,15,16-trihydroxy-20-methyl-5-cis, 13-trans, 17-trans-prostatrienoate.

12. The compound according to claim 3 dl-erythro-9-oxo-11α,15epi,16-trihydroxy-20-methyl-5-cis-13-trans-17-trans prostatrienoic acid.

13. The compound according to claim 3 nat-erythro-9-oxo-11α,15epi,16-trihydroxy-20-methyl-5-cis-13-trans-17-trans prostatrienoic acid.

14. The compound according to claim 3 dl-erythro-methyl 9-oxo-11α,15epi,16-trihydroxy-20-methyl-5-cis-13-trans, 17-trans-prostatrienoate.

15. The compound according to claim 3 nat-erythro-methyl 9-oxo-11α,15epi,16-trihydroxy-20-methyl-5-cis-13-trans, 17-trans-prostatrienoate.

16. The compound according to claim 3, nat.-erythro, 9-oxo-11α,15-epi,16-trihydroxy-5-cis-13-trans,-17-trans-prostatrienoic acid.

17. The compound according to claim 3, d,1-erythro-methyl-9-oxo-11α,15-epi,16-trihydroxy-5-cis-13-trans-17-trans-prostatrienoate.

* * * * *